US00PP32027P2

(12) United States Plant Patent
Kievit

(10) Patent No.: US PP32,027 P2
(45) Date of Patent: Jul. 28, 2020

(54) ***SALVIA* PLANT NAMED 'PURPLE AND BLOOM'**

(50) Latin Name: ***Salvia* hybrid**
Varietal Denomination: Purple and Bloom

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/602,336

(22) Filed: Sep. 16, 2019

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

(56) References Cited

PUBLICATIONS

The National Gardening Association Plant Database Mar. 26, 2020 pp. 1-6.*

* cited by examiner

*Primary Examiner* — Annette H Para
(74) *Attorney, Agent, or Firm* — Audrey Charles

(57) ABSTRACT

A new and distinct cultivar of *Salvia* plant named 'Purple & Bloom', characterized by its dark violet-colored flowers, dark green-colored foliage, and vigorous, upright growth habit, is disclosed.

1 Drawing Sheet

Latin name of genus and species of plant claimed: *Salvia* hybrid.

Variety denomination: 'Purple & Bloom'.

BACKGROUND OF THE INVENTION

The present invention relates to a new and distinct cultivar of *Salvia* plant botanically known as *Salvia* hybrid and hereinafter referred to by the cultivar name 'Purple & Bloom'.

The new cultivar originated in a controlled breeding program in Hem, the Netherlands during August 2014. The objective of the breeding program was the development of *Salvia* cultivars having large flowers with attraction coloration, dark green-colored foliage, and a vigorous, highly branched, upright growth habit.

The new *Salvia* cultivar is the result of cross-pollination. The female (seed) parent of the new cultivar is Vista Red & White 'PAS3287', not patented, characterized by its red and white bicolored flowers, dark green-colored foliage, and moderately vigorous, compact, columnar-upright growth habit. The male (pollen) parent of the new cultivar is 'Blue Enigma', not patented, characterized by its deep blue-colored flowers, dark green-colored foliage, and vigorous, upright growth habit. The new cultivar was discovered and selected as a single flowering plant within the progeny of the above stated cross-pollination during March 2015 in a controlled environment in Hem, the Netherlands.

Asexual reproduction of the new cultivar by terminal stem cuttings since March 2015 in Hem, the Netherlands and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Purple & Bloom' as a new and distinct cultivar of *Salvia* plant:

1. Dark violet-colored flowers;
2. Dark green-colored foliage; and
3. Vigorous, upright growth habit.

Plants of the new cultivar differ from plants of the female parent primarily in having dark violet-colored flowers and a more vigorous growth habit. Plants of the new cultivar differ from plants of the male parent primarily in having dark violet-colored flowers and a shorter, more branched growth habit.

Of the many commercially available *Salvia* cultivars, the most similar in comparison to the new cultivar is the male parent Black & Bloom, U.S. Plant Pat. No. 27,183. However, in side-by-side comparisons, plants of the new cultivar differ from plants of 'Black & Bloom' in at least the following characteristics:

1. Plants of the new cultivar have flowers with less blue coloration than plants of 'Black & Bloom'; and
2. Plants of the new cultivar have lighter colored bracts than plants of 'Black & Bloom'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Purple & Bloom'. The plants were approximately 3.5 months old and grown in 6-inch pots for approximately 8 weeks in a greenhouse in West Chicago, Ill. Plants were given one pinch 3 weeks after sticking.

DETAILED BOTANICAL DESCRIPTION

Figure 1:
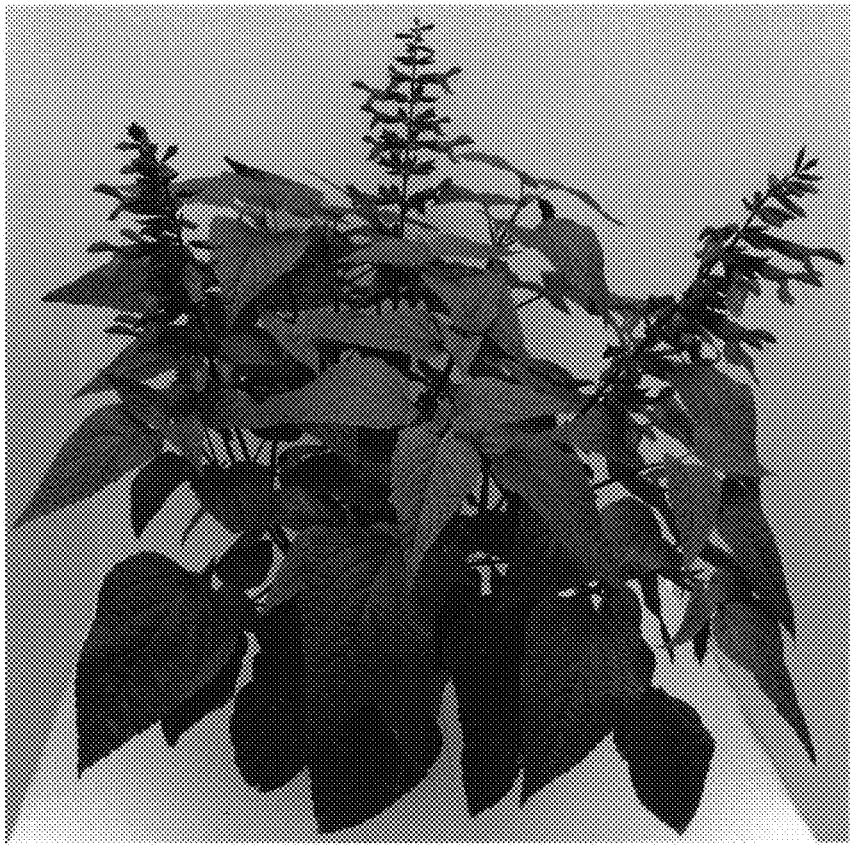
FIG. 1 illustrates a side view of the overall growth and flowering habit of 'Purple & Bloom'.
Figure 2:
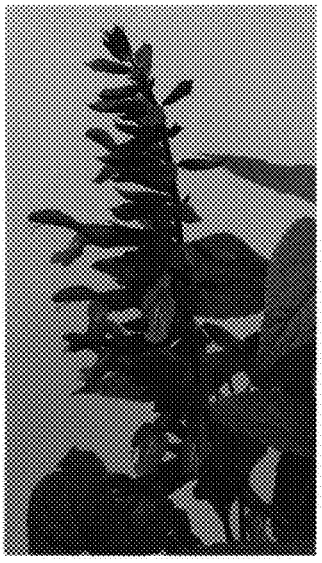
FIG. 2 illustrates a close-up view of an inflorescence of 'Purple & Bloom'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2019 under natural light conditions in West Chicago, Ill.

The following descriptions and measurements describe approximately 4-month old plants produced from cuttings from stock plants and grown in a glass-covered greenhouse under conditions comparable to those used in commercial practice. The plants were grown in West Chicago, Ill. in 6-inch pots for approximately 10 weeks utilizing a soilless growth medium. Plants were given one pinch 3 weeks after sticking. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Salvia* hybrid 'Purple & Bloom'.

Parentage:

*Female parent.*—Vista Red & White 'PAS3287', not patented.

*Male parent.*—'Blue Enigma', not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Medium thickness, fibrous, brown in color.

*Rooting habit.*—Freely branching.

Plant description:

*Commercial crop time.*—Approximately 8 to 10 weeks from a rooted cutting to finish in a 15 cm pot.

*Growth habit and general appearance.*—Vigorous, upright growth habit.

*Size.*—Height from soil level to top of plant plane: Approximately 52.0 cm. Width: Approximately 59.0 cm.

*Branching habit.*—Freely branching. Pinching enhances lateral branching. Quantity of branches per plant: Approximately 2 main basal branches and approximately 14 lateral branches.

*Branch.*—Shape: Square in cross section. Strength: Strong. Length to base of inflorescence: Approximately 31.0 cm. Diameter: Approximately 6.0 mm. Length of central internode: Approximately 8.0 cm. Texture: Moderately pubescent. Color of young and mature stems: 146A with an overlay of N186B.

Foliage description:

*General description.*—Quantity of leaves per main branch: Approximately 10. Fragrance: Strong, sage-like. Form: Simple. Arrangement: Opposite.

*Leaves.*—Aspect: Acute to perpendicular angle to stem. Shape: Ovate to deltoid. Margin: Crenate. Apex: Acute. Base: Truncate to slightly oblique. Venation pattern: Pinnate. Length of mature leaf: Approximately 14.0 cm. Width of mature leaf: Approximately 9.5 cm. Texture of upper surface: Rugose, sparsely pubescent. Texture of lower surface: Rugose, densely pubescent. Color of upper surface of young foliage: 137A with 139A and venation of 147B. Color of lower surface of young foliage: Closest to NN137D with venation of 146C. Color of upper surface of mature foliage: NN137A with 139A and venation of 147B. Color of lower surface of mature foliage: Closest to NN137D with venation of 146C, midvein has a heavy overlay of N186C nearest petiole attachment fading at midpoint toward apex.

*Petiole.*—Length: Approximately 7.0 cm. Diameter: Approximately 4.0 mm. Texture: Moderately pubescent. Color: 146A with a heavy overlay of N186B.

Flowering description:

*Flowering habit.*—'Purple & Bloom' is freely flowering under outdoor growing conditions with substantially continuous blooming from spring through autumn and year-round in greenhouse environment.

*Lastingness of individual floret.*—Approximately 4 to 5 days.

Inflorescence description:

*General description.*—Type: Spikes in verticillaster arrangement, florets in clusters of five, not persistent. Quantity of inflorescences per plant: Approximately 10. Fragrance: Faint, sweet. Length or height of inflorescence: Approximately 24.0 cm. Width of inflorescence: Approximately 9.5 cm. Quantity of fully-open flowers per inflorescence: Approximately 14.

*Peduncle.*—Shape: Square in cross section. Strength: Strong. Aspect: Erect. Length: Approximately 5.5 cm. Diameter: Approximately 4.0 mm. Texture: Densely glandular pubescent. Color: N186B.

Flower description:

*Type.*—Single, zygomorphic.

*Bud.*—Rate of opening: Generally takes 2 to 3 days for bud to progress from first color to fully open flower.

*Bud just before opening.*—Shape: Obovoid. Length: Approximately 1.8 cm. Diameter: Approximately 6.0 mm. Texture: Moderately pubescent. Color: Calyx of N92A and petals of N92C.

*Corolla.*—Shape: Bilabiate, lower lip having three lobes, base fused. Width: Approximately 1.0 cm. Length: Approximately 3.2 cm. Depth: Approximately 4.6 cm.

*Upper lip.*—Shape: Hooded. Margin: Entire. Apex: Rounded. Length from throat: Approximately 2.0 cm. Width: Approximately 4.0 mm. Texture of inner surface: Glabrous. Texture of outer surface: Moderately pubescent. Color of inner surface when first and fully open: 86B. Color of outer surface when first and fully open: 86A with N87A.

*Lower lip.*—Shape of central lobes: Oblong. Margin: Entire. Apex of central lobe: Emarginate. Apex of lateral lobes: Rounded. Length from throat of central lobe: Approximately 1.7 cm. Width of central lobe: Approximately 6.0 mm. Length from throat of lateral lobes: Approximately 1.4 cm. Width of lateral lobes: Approximately 2.0 mm. Texture of upper surface: Glabrous. Texture of lower surface: Sparsely pubescent. Color of upper surface when first and fully open: 86A and N87A with two central patches of NN155D near throat opening. Color of lower surface when first and fully open: 86B.

*Corolla tube.*—Length: Approximately 2.0 cm. Diameter at opening: Approximately 3.0 mm. Diameter at base: Approximately 2.0 mm. Texture of inner and outer surfaces: Glabrous. Color of inner surface when first and fully open: N87D with base of NN155D. Color of outer surface when first and fully open: 86A and N87A with base of NN155D.

*Calyx.*—Shape: Tubular. Length: Approximately 2.0 cm. Diameter: Approximately 6.0 mm.

*Sepals.*—Quantity per flower: Fused into two lobes. Shape: Obovate. Apex: Upper lobe acute, lower lobe notched. Length: Approximately 2.0 cm. Width of lobes: Approximately 6.0 mm. Texture of inner and outer surfaces: Moderately pubescent. Color of inner surface: 146D with tips of N92A. Color of outer surface: 146A with a heavy overlay of N186A and N92A.

*Bracts.*—Quantity: One bract located at the base of floret cluster. Shape: Ovate. Apex: Acuminate. Length: Approximately 1.4 cm. Width: Approximately 6.0 mm. Texture of inner surface: Glabrous. Texture of outer surface: Moderately pubescent. Color of inner surface: NN155D with an overlay of 86B and tips of N92A. Color of outer surface: 86B and tips of N92A.

*Pedicel.*—Strength: Strong, flexible. Aspect: At an acute angle. Length: Approximately 7.0 mm. Diameter: Approximately 1.0 mm. Texture: Densely pubescent. Color: 146B with a heavy overlay of N186B.

*Reproductive organs.*—Androecium: Stamen quantity: 2 per flower, dorsifixed, strongly curved. Stamen length: Approximately 2.4 cm. Filament length: Approximately 2.0. Filament color: NN155D with lower half of 86A and N92A. Anther shape: Oblong. Anther length: Approximately 4.0 mm. Anther color: N92C. Pollen amount: Abundant. Pollen color: NN155A. Gynoecium: Pistil quantity: 1 per flower, slightly curved. Pistil length: Approximately 4.5 cm. Stigma shape: Cleft, two-parted. Stigma length: 4.0 mm. Stigma color: 86A. Style length: Approximately 3.8 cm. Style color: NN155D with an overlay of 86B near stigma. Style texture: One longitudinal line of hairs colored 86B. Ovary length: Approximately 3.0 mm. Ovary color: 18D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Purple & Bloom', substantially as herein illustrated and described.

* * * * *